United States Patent [19]

Zlock et al.

[11] Patent Number: 5,405,072
[45] Date of Patent: Apr. 11, 1995

[54] ANVIL FOR SURGICAL STAPLERS

[75] Inventors: Stephen W. Zlock, Hawthorne, N.Y.; Donald Morin, Litchfield, Conn.

[73] Assignee: United States Surgical Corporation, Norwalk, Conn.

[21] Appl. No.: 149,127

[22] Filed: Nov. 5, 1993

Related U.S. Application Data

[63] Continuation of Ser. No. 777,998, Oct. 17, 1991, abandoned.

[51] Int. Cl.6 ............................................. A61B 17/068
[52] U.S. Cl. ........................................ 227/175; 227/19
[58] Field of Search ............... 227/175, 176, 177, 178, 227/179, 180, 181, 182, 19, 76, 152, 153

[56] References Cited

U.S. PATENT DOCUMENTS

| | | | |
|---|---|---|---|
| D. 322,143 | 12/1991 | Spreckelmeier | D24/145 |
| 3,079,606 | 3/1963 | Bobrov et al. | 227/76 |
| 3,490,675 | 1/1970 | Green et al. | 227/19 |
| 3,499,591 | 3/1970 | Green | 227/19 X |
| 4,111,206 | 9/1978 | Vishnevsky et al. | 227/19 X |
| 4,244,372 | 1/1981 | Kapitanov et al. | 227/180 X |
| 4,290,542 | 9/1981 | Fedotov et al. | 227/155 |
| 4,429,695 | 2/1984 | Green | 128/305 |
| 4,520,817 | 6/1985 | Green | 227/176 |
| 4,520,817 | 6/1985 | Green | 128/305 |
| 4,617,928 | 10/1986 | Alfranca | 128/305 |
| 4,633,861 | 1/1987 | Chow et al. | 128/305 |
| 4,633,874 | 1/1987 | Chow et al. | 227/176 |
| 4,784,137 | 11/1988 | Kulik et al. | 128/334 R |
| 4,863,088 | 9/1989 | Redmond et al. | 227/19 |
| 4,892,244 | 1/1990 | Fox et al. | 227/8 |
| 4,955,959 | 9/1990 | Tompkins et al. | 227/178 |
| 5,014,899 | 5/1991 | Presty et al. | 227/180 |
| 5,030,111 | 7/1991 | Eastman | 439/470 |
| 5,065,929 | 11/1991 | Schulze et al. | 227/19 |
| 5,074,454 | 12/1991 | Peters | 227/19 X |
| 5,111,987 | 5/1992 | Moeinzadeh et al. | 227/176 X |

FOREIGN PATENT DOCUMENTS

| | | |
|---|---|---|
| 0178941 | 4/1986 | European Pat. Off. |
| 0179623 | 4/1986 | European Pat. Off. |
| 0246870 | 11/1987 | European Pat. Off. |
| 0332413 | 9/1989 | European Pat. Off. |
| 2445132 | 7/1980 | France. |
| 1198666 | 7/1970 | United Kingdom. |

OTHER PUBLICATIONS

The ILA Stapler Brochure, 3M Catalogue, publication date unknown, copyright Sep. 1987.

*Primary Examiner*—Ricahrd K. Seidel
*Assistant Examiner*—Raymond D. Woods

[57] ABSTRACT

An anvil for use in surgical fastener applying apparatus includes an indentation extending lengthwise along at least one of the side walls to provide increased resistance to bending and to permit the application of longer rows of fasteners. An added feature is the deflection preventing member which projects laterally from the side of the anvil and which engages and abuts a corresponding notch in the apparatus for preventing flexure of the anvil when the fastener is closed onto body tissue.

39 Claims, 3 Drawing Sheets

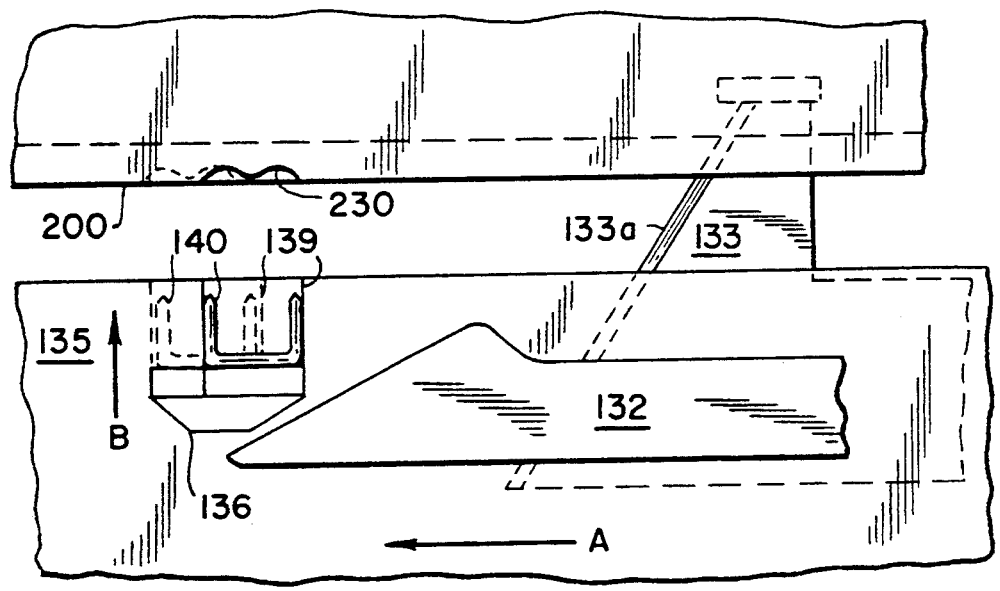
FIG.2
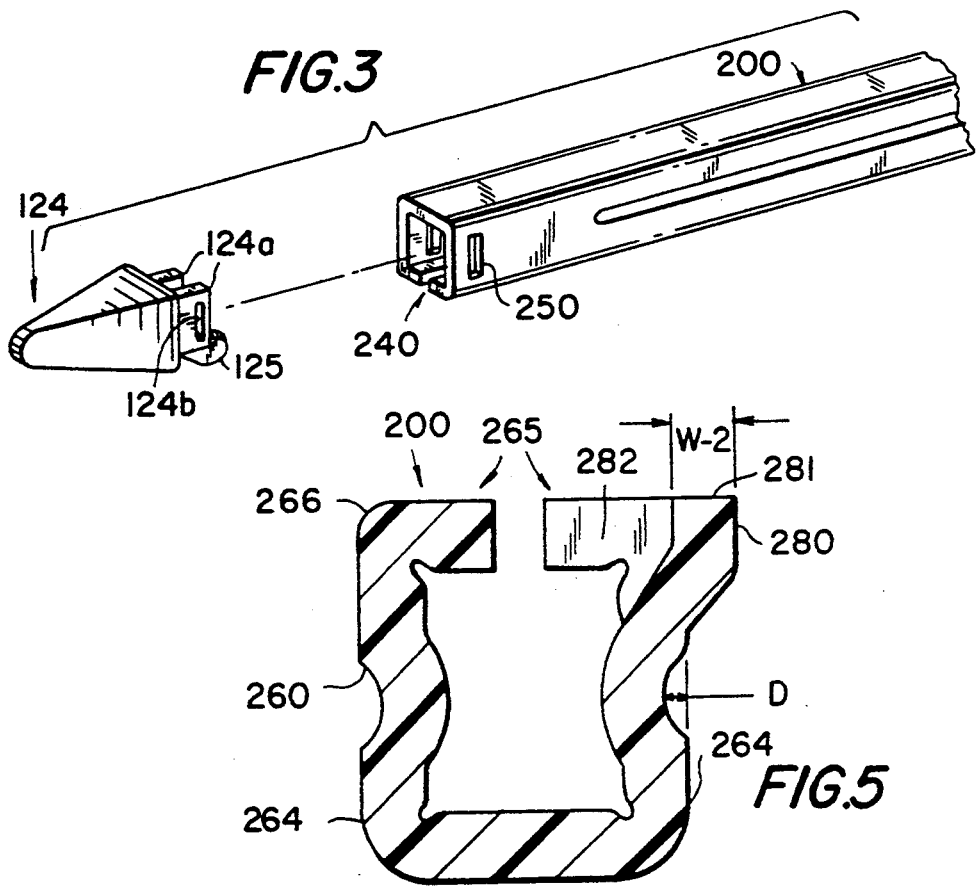
FIG.3
FIG.5

ANVIL FOR SURGICAL STAPLERS

This is a continuation of application Ser. No. 07/777,998, filed on Oct. 17, 1991, and now abandoned.

BACKGROUND OF THE INVENTION

1. Field of the Invention

The present invention relates to surgical instruments for applying rows of fasteners to body tissue, and more particularly to anvil members employed in such instruments.

2. Background of the Art.

Surgical fastener applying instruments used for applying parallel rows of fasteners to body tissue are well known in the art and are commonly used for transecting or reconnecting body tissue such as intestinal, gastric, or lung tissue. The fasteners can be in the form of staples which are closed by crimping the staple legs, or two part fasteners which are closed by locking together a fastener portion with a retainer portion.

Surgical staple applying instruments are illustrated and described, for example, in U.S. Pat. Nos. 4,633,861; 4,633,874; 4,863,088; 3,079,606; 3,490,675; 3,499,591; and 4,429,695. Generally, such staplers include a forked distal end. The body tissue to be operated upon is held securely between two forks of the instrument and the staples are sequentially applied to the tissue.

One fork comprises staple holding and pushing means. Usually, at least two parallel rows of staples are held in slots oriented transversely to the longitudinal axis of the instrument. Pusher elements are located behind the staples. When a camming bar is moved longitudinally by a drive member the pusher elements are driven through the slots, thereby pushing the staples out into the body tissue. The other fork comprises an anvil, i.e., staple closing means. The legs of the staple penetrate the body tissue and enter staple closing depressions in the anvil where they are crimped.

The surgical fasteners must be properly closed to insure that the body tissue is securely fastened, otherwise bleeding or other complications can occur from poor hemostasis of the fastened tissue. Proper closure of the fasteners requires precise alignment of the two forks of the instrument so that the fasteners are precisely aligned with the closing means. However, bending or deflection of the anvil can occur when the two forks are clamped together with body tissue in between, and this bending can cause misalignment of the staples and the staple closing depressions. Deflection can also occur as a result of vertical forces applied to the anvil during contact by the fasteners. More deflection occurs at the distal end of the anvil. The longer the anvil the greater is the tendency to bend. Hence, one way of dealing with bending is to limit the length of the anvil. But in many applications it is desirable to use a longer anvil, which would be able to lay down longer rows of staples.

Another way of reducing bending is to make the anvil stronger. Anvils are presently fabricated by cold working sheet stainless steel of about 0.05 inches to about 0.075 inches in thickness into the desired shape. Stronger anvils can be made by increasing the thickness of the steel. However, this presents disadvantages insofar as the weight and cost of the anvil, as well as the difficulty of working thicker steel, are increased. Using an alternative, harder material of construction can increase the rigidity of the anvil, but possibly at the expense of sacrificing desirable properties of the stainless steel. Therefore, the need exists to fabricate an anvil which is stronger and more resistant to bending while avoiding the disadvantages just mentioned.

SUMMARY OF THE INVENTION

Provided herein is an anvil member for use in apparatus for applying a plurality of surgical fasteners to body tissue. The apparatus includes fastener holder means for carrying a plurality of surgical fasteners in at least two parallel rows, and means responsive to user applied force and movable generally along the longitudinal axis of the apparatus for driving said fasteners from said fastener holder means into a fastener closing surface of the elongated anvil member. The rows of fasteners are aligned with the longitudinal axis of the apparatus and the fasteners are sequentially driven from said fastener holder in a direction transverse to the longitudinal axis of the apparatus by a longitudinally moving cam bar. The anvil is an elongated member including at least one each of lengthwise extending first and second walls generally defining mutually transverse respective planes and each having a distal portion and a proximal portion, the distal portion of said first wall including means for closing the surgical fasteners, and said second wall having at least one elongated indentation extending lengthwise thereon.

A complementary feature to prevent flexing of the anvil when the apparatus is closed onto body tissue includes a deflection preventing member projecting laterally from the proximal portion of the anvil.

BRIEF DESCRIPTION OF THE DRAWINGS

FIG. 2 is an elevational view of a portion of the cartridge assembly.

FIG. 3 is an exploded perspective view of the anvil tip.

FIG. 5 is a sectional view of the anvil member illustrating the deflection preventing member.

DETAILED DESCRIPTION OF PREFERRED EMBODIMENT(S)

A surgical stapler employing the anvil of the present invention is generally of similar construction to the surgical stapler disclosed in U.S. Pat. No. 5,014,899, which is herein incorporated by reference in its entirety.

Figure 1:
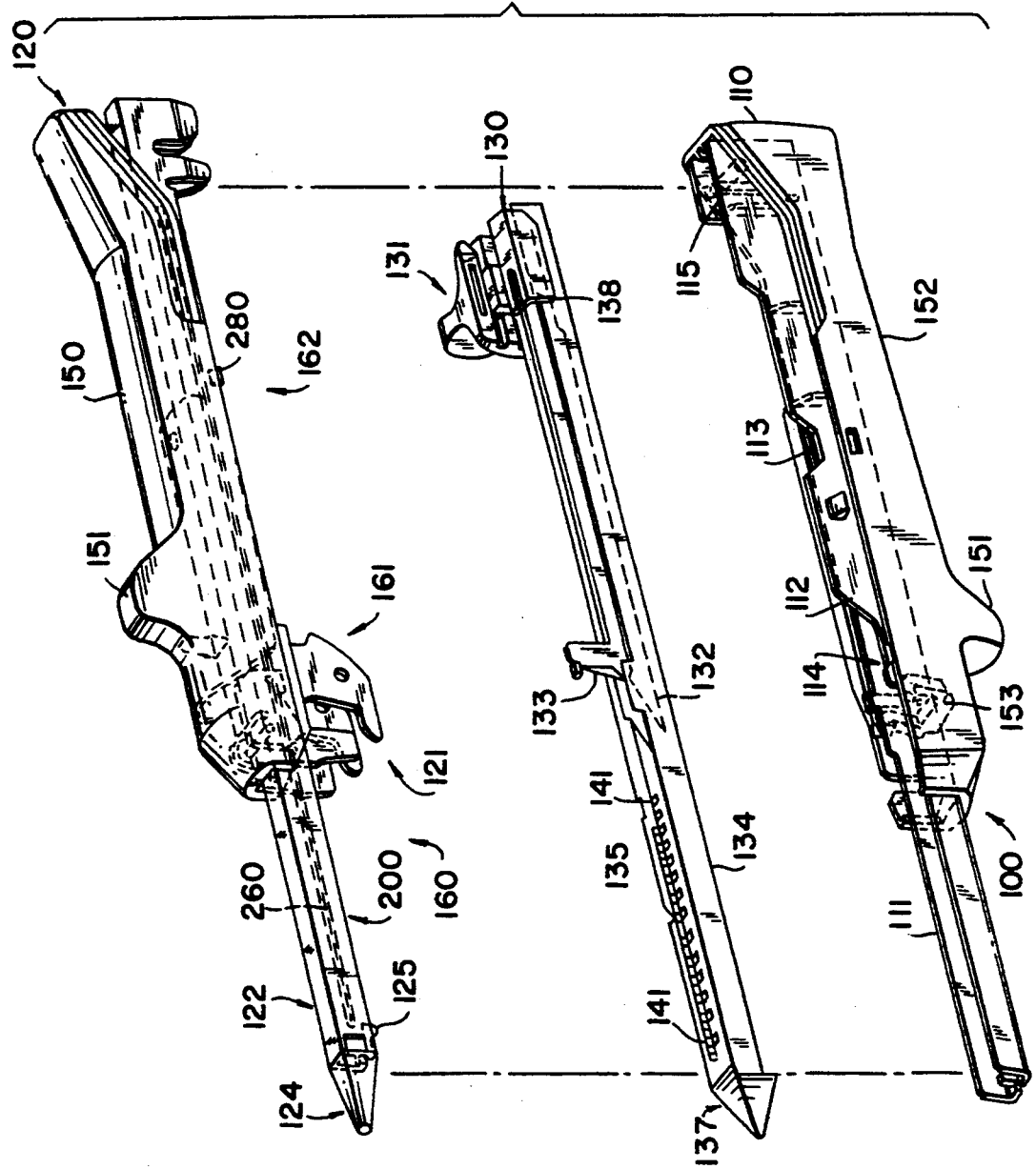
FIG. 1 is an exploded perspective view of the fasteners applying apparatus of the present invention.

Referring to FIG. 1, the surgical stapling apparatus 100 of the present invention comprises a first frame 110 including cartridge support 114 which has a distal projection 111 for holding a cartridge assembly, a finger rest 151, a stationary handle 152, locking bar 153, a side plate 112, and a notch 113 in the side plate 112. A cylindrical crosspiece 115 extends laterally across first frame in proximity to the proximal end of the apparatus. A second frame 120 has a pair of hinge plates 121 for hingedly connecting to the first frame 110, a pivotable handle 150, a finger rest 151, and a distal projection 122 comprising an anvil assembly 200. Hinge plates 121 apply leverage force to locking bar 153 to secure the frames 110 and 120 together for assembly. The anvil assembly 200 is formed of a plate with indentations or depressions 230 as shown more clearly in FIG. 4, for crimping the legs of metal staples. Alternatively, the anvil assembly may include means for holding rows of retainer portions of two-part surgical fasteners to facilitate mutual engagement of the fastener and retainer portions of the two-part fasteners. Tip 124 allows distal projection 122 to be more easily positioned in body tissue. The resilient deflectable arm 125 is preferably attached to tip 124. Deflectable arm 125 may be formed integral with the tip 124, or it may be in the form of a separate attachment.

The apparatus 100 and its longitudinally extending parts may be conceptually divided along their length into three portions: a distal portion 160 which extends distally beyond the handle member 150 and 152, a middle portion 161 in the vicinity of hinge plates 121 and locking bar 153 where the leverage forces are applied during assembly of the apparatus, and a proximal portion 162 generally proximal to the finger rests 15 1.

Actuating assembly 130 for driving the surgical fasteners is a replaceable insert which includes a pusher assembly having a thrust knob 131, cam bars 132, and knife blade 133. The actuating assembly or insert 130 further includes a stationary carder 134 for holding cartridge assembly 135. Tip 137 at the distal end of the cartridge assembly facilitates positioning body tissue for fastening. Referring also to FIG. 2, cartridge assembly 135 includes pusher members 136 for pushing surgical fasteners out from their respective slots and into contact with the anvil for closure. Cam bars 132 and knife 133 are mounted at their proximal ends to cam bar retainer 138, which is connected to the thrust knob 131 and which provides a means for transferring manually applied force from the thrust knob 131 to the cam bars 132.

In operation the insert 130 is loaded into the first frame 110, and the instrument is then assembled such that the body tissue to be operated upon is located between the cartridge assembly 135 and the anvil 200. The knife 133 is positioned such that it can simultaneously move along slot 240 (see FIG. 4) in the anvil 200 and slot 141 (FIG. 1) in the cartridge assembly. The instrument is then fired by the surgeon's pressing forward (i.e., distally) on the thrust knob 131.

Referring again to FIG. 2, the cam bars 132 and knife 133 are then moved distally and longitudinally along the instrument in the direction indicated by arrow A. The knife 133 creates an incision in the body tissue (not shown) by means of its distal cutting edge 133a, and the cam bars 132 drive the fastener pushers 136 in a direction indicated by arrow B, which is transverse to that of the longitudinal axis of the instrument. The pushers 136, in turn, drive the fasteners 140 out of their slots 139 and into the depressions 230 in the anvil plate for crimping, thereby fastening the tissue on both sides of the incision. When the operation is completed the used replaceable insert 130 can be disposed, and a new one installed in the apparatus.

FIG. 3 illustrates the anvil tip 124 having prongs 124a and detents 124b on the outer sides of the prongs. The detents 124b are for engaging side slots 250 (See FIG. 4) in the anvil 200.

Figure 4:
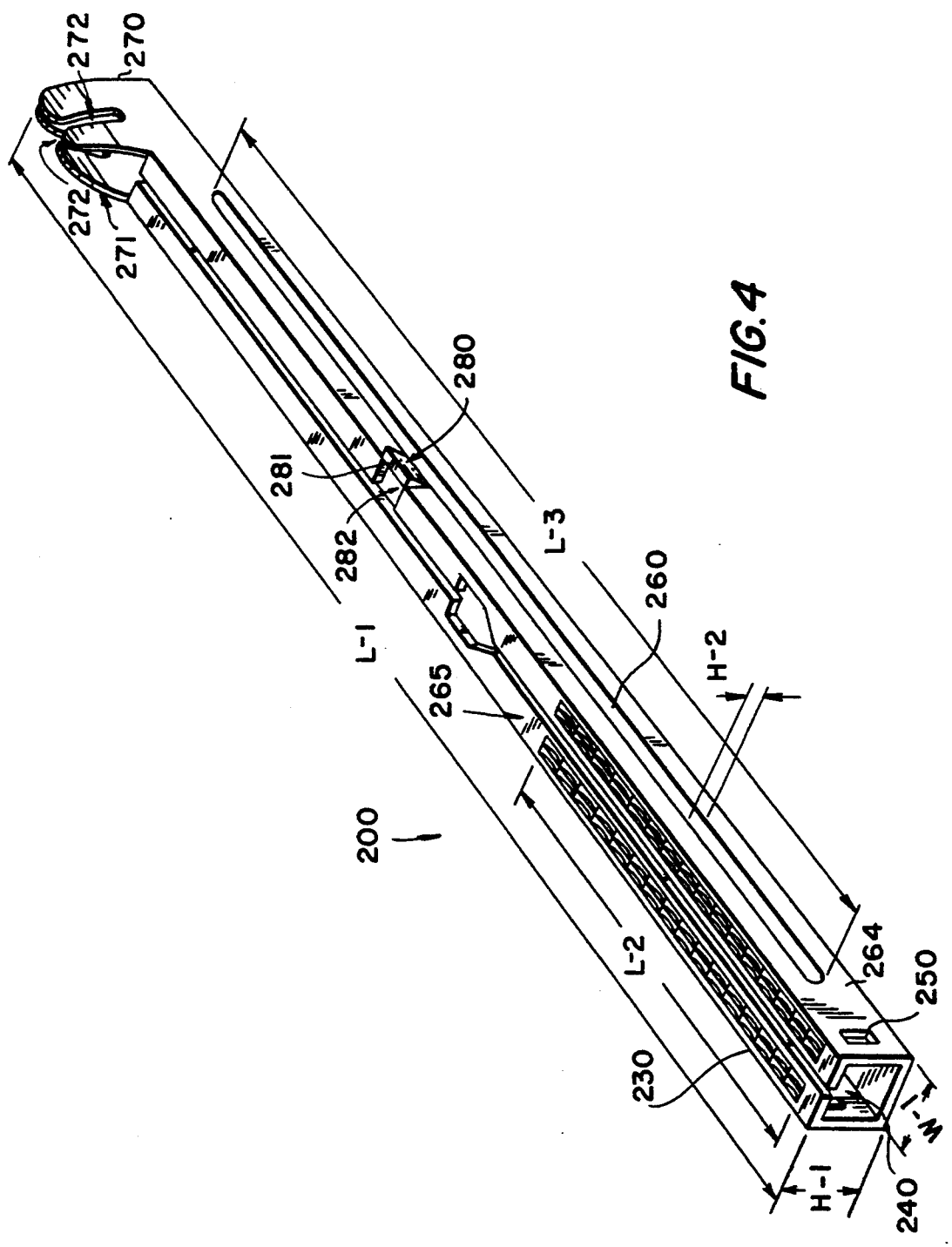
FIG. 4 is a perspective view of the anvil member of the present invention.

Referring to FIG. 4, anvil 200 is preferably fabricated from 305 stainless steel sheet of from about 0.068 to about 0.072 inches in thickness. Wall 265 defines a planar tissue contacting surface and contains fastener closing means which can be staple closing depressions 230, as shown, or means for releasably holding the retainer portions of two-part surgical fasteners. Walls 264 are side walls which intersect with wall 265 to define ridges 266 (See FIG. 5), and which define planes transverse to the plane of wall 265. The anvil 200 includes a longitudinal indentation 260 extending along at least one, and preferably both, of the sides 264 adjacent to the tissue contacting surface 265 containing the staple closing depressions 230. The indentation 260 increases the strength of the anvil to reduce deflection during clamping of the body tissue between the anvil jaw and the staple jaw and during firing of the fasteners. The indentation 260 is illustratively centered on each side wall 264.

By way of example, the anvil 200 can have a length L-1 of from about 10.30 to about 10.50 inches, a height H-1 of about 0.35 to about 0.36 inches, and a width W-1 of from about 3.5 to about 3.6 inches. The elongated indentation 260 can have a length L-3 of preferably from 85% to 90% of the length L-1 of the anvil, i.e., from about 9.1 to 9.2 inches. Alternatively, the indentation can extend the entire length of the anvil. The depth D (FIG. 5) of the indentation 260 is preferably from about 0.020 inches to about 0.030 inches. The height H-2 is preferably from about 0.085 to 0.09 about inches. The length L-2 of the rows of staple forming depressions can be up to about from 3.0 to 3.5 inches. These dimensions axe illustrative and represent the size of but one embodiment of the present invention. Anvils of other dimensions are within the scope of the present invention.

The proximal end 270 of the anvil includes upright portions 271 including notch 272 for receiving crosspiece 115 in the first frame 110 to facilitate properly aligned engagement of the first and second frames when assembled.

The anvil 200 of the present invention further includes a deflection preventing member 280 located in the proximal portion 162 of the anvil. Deflection preventing member 280 has an upper abutment surface 281 and projects laterally beyond the side of the anvil. In one embodiment, the member 280 can extend a distance W-2 of about 0.065 inches to about 0.075 inches. The abutment surface 281 optionally can be flush with the tissue contacting surface 265. A notch 282 is located next to the deflection preventing member 280.

Referring to FIGS. 1, 4 and 5, the cartridge support 114 includes an upraised side plate 112 having a notch 113 for cooperatively engaging the deflection preventing member 280. When the apparatus is assembled for use, the abutment surface 281 abuts the bottom of notch 113 thereby preventing flexing of the anvil 200. The deflection preventing member is illustratively located about 3.5 inches from the proximal end 270 of the anvil, which is about midway between the middle portion 161 of the anvil and the proximal end 270.

When the instrument is closed by assembling the frames 120 and 110, and pivoting handle 150 down to secure the hinge plates 121 to the locking bar 153, the deflecting member 280 contacts the bottom edge of notch 113 and acts as a stop. This prevents bending of the proximal portion of the anvil 280, and thereby allowing a greater clamping force to be exerted at the distal end. Additionally, by functioning as a stop in the proximal portion of the anvil, the clamping leverage forces developed by the hinge plates and locking bar 153 are to a greater degree directed to the distal portion of the apparatus where the tissue is clamped, because the proximal portion of the anvil is prevented from flexing. Thus, the present invention encompasses both means for preventing bending of the anvil and for increasing clamping forces on the tissue.

While the above description contains many specifics, these specifics should not be construed as limitations of the scope of the invention, but merely as exemplifications of preferred embodiments thereof. Those skilled in the art will envision many other possible variations that are within the scope and spirit of the invention as defined by the claims appended hereto.

What is claimed is:

1. An anvil assembly for use in apparatus for applying a plurality of surgical fasteners to body tissue, which comprises:

an elongated assembly comprising first, second, third and fourth walls, two of said walls being generally transverse respective to a remaining two of said walls and said walls each having a distal portion and a proximal portion and a length, the distal portion of said first wall including means for closing the surgical fasteners, and said second wall having opposite facing interior and exterior surfaces and at least one elongated indentation located a distance from said first wall, said elongated indentation having a length and extending lengthwise along one of said interior and exterior surfaces of said second wall.

2. The anvil assembly of claim 1, wherein the length of said elongated indentation is from about 85% to about 90% of tile length of the second wall.

3. The anvil assembly of claim 1, wherein said means for closing said surgical fasteners comprises a plurality of depressions arranged in at least two parallel rows.

4. The anvil assembly of claim 1, further including a lengthwise extending slot in said first wall for permitting passage therethrough of a knife blade.

5. The anvil assembly of claim 1, further including abutment means to prevent flexing of a proximal portion of said anvil assembly.

6. The anvil assembly of claim 5, wherein said abutment means comprises a deflection preventing member projecting laterally from the proximal portion of said second wall and having an abutment surface.

7. The anvil assembly of claim 6, wherein said abutment surface is approximately flush with said first wall of the anvil assembly.

8. The anvil assembly of claim 7, wherein said anvil assembly is fabricated from stainless steel.

9. Apparatus for applying a plurality of surgical fasteners to body tissue, which comprises:

fastener holder means for carrying said plurality of surgical fasteners in at least two parallel rows;

means responsive to user applied force and movable generally along a longitudinal axis of the apparatus for driving said surgical fasteners from said fastener holder means into a fastener closing surface of an elongated anvil assembly;

said anvil assembly comprising first, second, third and fourth walls, two of said walls being generally transverse respective to a remaining two of said walls, each wall having a distal portion and a proximal portion and a length, the distal portion of said first wall including said fastener closing surface, and said second wall having opposite facing interior and exterior surfaces and at least one elongated indentation extending lengthwise thereon a distance from said first wall along one of said interior and exterior surfaces.

10. The apparatus of claim 9, wherein said surgical fasteners comprise generally U-shaped deformable staples and said fastener closing surface includes a plurality of indentations arranged in at least two parallel rows for crimping the staples.

11. The apparatus of claim 9, further including a lengthwise extending slot in said first wall of said anvil assembly for permitting passage therethrough of a knife blade.

12. The apparatus of claim 9, wherein said anvil assembly further includes abutment means to prevent flexing of said anvil assembly.

13. The apparatus of claim 12, wherein said abutment means comprises a deflection preventing member projecting laterally from the proximal portion of said second wall and having an abutment surface.

14. The apparatus of claim 13, wherein said abutment surface is approximately flush with said first wall of the anvil assembly.

15. The apparatus of claim 9, wherein said rows of fasteners are aligned with the longitudinal axis of the apparatus and wherein said fasteners are sequentially driven from said fastener holder means in a direction transverse to the longitudinal axis of the apparatus by a longitudinally moving cam bar.

16. An apparatus for applying a plurality of surgical fasteners to body tissue which includes fastener holding means for carrying a plurality of surgical fasteners in at least two parallel rows; and means responsive to user applied force and movable generally along a longitudinal axis of the apparatus for driving said surgical fasteners from said fastener holding means into a fastener closing surface of an elongated anvil member, said anvil member having at least one side wall oriented orthogonally to said fastener closing surface and having a length and lengthwise extending interior and exterior surfaces, and at least one elongated convex protrusion extending lengthwise along, and protruding from, one of said interior and exterior surfaces of said side wall of said anvil member for preventing bending of the anvil member, wherein said convex protrusion is located at a distance from said fastener closing surface.

17. The apparatus of claim 16, wherein said apparatus includes support means for supporting said fastener holding means, said support means including a side plate with a stop surface, and wherein said anvil member includes a projection having an abutment surface for contacting said stop surface and preventing bending of the anvil member.

18. The apparatus of claim 16, wherein said protrusion protrudes from said interior surface of the side wall of the apparatus.

19. An apparatus for applying a plurality of surgical fasteners to body tissue which includes;

fastener holding means for carrying said plurality of surgical fasteners in at least two parallel rows; means responsive to user applied force and movable generally along a longitudinal axis of the apparatus for driving said surgical fasteners from said fastener holding means into a fastener closing surface of an elongated anvil member, said anvil member having at least one side wall oriented orthogonally to said fastener closing surface and having a length and opposite facing lengthwise extending interior and exterior surfaces; and, at least one elongated indentation extending lengthwise along one of said interior and exterior surfaces of said side wall for preventing bending of the anvil member.

20. The apparatus of claim 19 wherein said indentation is located a distance from said fastener closing surface.

21. The apparatus of claim 19 wherein said wall possesses an elongated convex portion on the interior surface of the anvil member wall.

22. An apparatus for applying a plurality of surgical fasteners to body tissue, which comprises:
   fastener holding means for carrying said plurality of surgical fasteners in at least two parallel rows; and
   means responsive to user applied force and movable generally along a longitudinal axis of the apparatus for driving said surgical fasteners from said fastener holding means into a fastener closing surface of an elongated anvil member,
   said anvil member having at least one side wall oriented orthogonally to said fastener closing surface and having a length and opposite facing lengthwise extending interior and exterior surfaces, and at least one elongated protrusion extending lengthwise along, and protruding from, one of said interior and exterior surfaces of said side wall of said anvil member for preventing bending of the anvil member, wherein said protrusion comprises a convex surface corresponding to an elongated concave indentation extending along said side wall on the other of said interior and exterior surfaces.

23. An anvil for use in apparatus for applying a plurality of surgical fasteners to body tissue, which comprises:
   an elongated member including at least one each of lengthwise extending first and second walls generally defining mutually transverse respective planes and each having a distal portion and a proximal portion, the distal portion of said first wall including means for closing the surgical fasteners, and said second wall having an externally facing surface and at least one elongated indentation extending lengthwise thereon.

24. The anvil of claim 23 wherein the length of said elongated indentation is at least about 85% of the length of the second wall.

25. The anvil of claim 24 wherein the length of said elongated indentation is from about 85% to about 90% of the length of said second wall.

26. The anvil of claim 23 wherein
   said elongated member has a longitudinally extending slot in said first wall for permitting passage therethrough of a knife blade.

27. The anvil of claim 26 further including abutment means to prevent flexing of a proximal portion of said anvil, wherein said abutment means comprises a deflection preventing member projecting laterally from the proximal portion of said second wall and having an abutment surface.

28. The anvil of claim 27 wherein said abutment surface is approximately flush with said first wall of the anvil.

29. The anvil of claim 28 wherein said anvil is fabricated from stainless steel.

30. Apparatus for applying a plurality of surgical fasteners to body tissue, which comprises:
   fastener holding means for carrying a plurality of surgical fasteners in at least two parallel rows;
   means responsive to user applied force and movable generally along a longitudinal axis of the apparatus for driving said surgical fasteners from said fastener holder means into a fastener closing surface of an elongated anvil assembly;
   said anvil assembly having a length and lengthwise extending first and second walls generally defining mutually transverse planes intersecting each other at a corner ridge and each having a distal portion and a proximal portion, the distal portion of said first wall including said fastener closing surface, and said second wall having at least one elongated indentation extending lengthwise thereon, and said anvil assembly further including a longitudinally extending slot in said first wall of said anvil assembly for permitting passage therethrough of a knife blade.

31. Apparatus for applying a plurality of surgical fasteners to body tissue, which comprises:
   fastener holding means for carrying said plurality of surgical fasteners in at least two parallel rows;
   means responsive to user applied force and movable generally along a longitudinal axis of the apparatus for driving said surgical fasteners from said fastener holder means into a fastener closing surface of an elongated anvil member;
   said anvil member having a length and at least one each of lengthwise extending first and second walls generally defining mutually transverse planes intersecting each other at a corner ridge and each having a distal portion and a proximal portion, the distal portion of said first wall including said fastener closing surface, said fastener closing surface defining a plane which is orthogonal to the plane defined by said second wall, and said second wall having at least one elongated indentation extending lengthwise thereon, wherein said anvil member further includes a deflection preventing member having an abutment surface projecting laterally from the proximal portion of said second wall to prevent flexing of the anvil member.

32. The apparatus of claim 31 wherein said abutment surface is approximately flush with said first wall of said anvil member.

33. An apparatus for applying at least two rows of surgical fasteners to body tissue comprising:
   a first elongate assembly having a first clamping surface, a second elongate assembly having a second clamping surface;
   said first and second elongate assemblies being movable from a first position wherein said clamping surfaces are spaced apart, to a second position for clamping said tissue and applying said surgical fasteners;
   said first elongate assembly having a first wall and a second wall, said first clamping surface located on said first wall, said second wall having a length and opposite facing interior and exterior surfaces extending lengthwise thereon, said first elongate assembly having an elongated indentation having a concave surface and spaced from said first wall and extending lengthwise along at least one of said interior and exterior surfaces of said second wall;
   means responsive to user applied force and movable generally along a longitudinal axis of the apparatus for driving said fasteners through said body tissue clamped between said elongate assemblies.

34. The apparatus of claim 33, wherein said indentation extends along said exterior surface of said second wall.

35. The apparatus of claim 33, wherein said indentation is adapted for preventing bending of the anvil member.

36. The apparatus of claim 33, wherein said indentation is defined by a concave portion of the exterior surface of the second wall.

37. The apparatus of claim 33, further including a longitudinally extending slot in each of said clamping surfaces for permitting passage therethrough of a knife blade.

38. The apparatus of claim 33, further comprising a third wall having a length and opposite facing interior and exterior surfaces extending lengthwise thereon, wherein said second wall and said third wall are in planes generally transverse to said first wall, and further comprising a second elongated indentation located a distance from said first wall and extending lengthwise along at least one of said interior and exterior surfaces of said third wall.

39. The apparatus of claim 38, wherein said elongated indentations are parallel and adapted to prevent flexing of said first elongate assembly during said clamping of tissue.

* * * * *